US008291753B2

(12) United States Patent
Range et al.

(10) Patent No.: US 8,291,753 B2
(45) Date of Patent: Oct. 23, 2012

(54) TIRE DEFECT TESTER

(75) Inventors: David E. Range, Elk River, MN (US);
Gary William Box, Golden Valley, MN (US)

(73) Assignee: Paul E. Hawkinson Company, Maple Grove, MN (US)

( * ) Notice: Subject to any disclaimer, the term of this patent is extended or adjusted under 35 U.S.C. 154(b) by 1091 days.

(21) Appl. No.: 12/129,462

(22) Filed: May 29, 2008

(65) Prior Publication Data
US 2009/0078034 A1    Mar. 26, 2009

Related U.S. Application Data

(60) Provisional application No. 60/932,310, filed on May 29, 2007.

(51) Int. Cl.
*G01M 17/02* (2006.01)
(52) U.S. Cl. .......................................... 73/146; 340/442
(58) Field of Classification Search ........................ None
See application file for complete search history.

(56) References Cited

U.S. PATENT DOCUMENTS

| | | | | | |
|---|---|---|---|---|---|
| 4,297,876 | A | * | 11/1981 | Weiss | 73/146 |
| 4,327,579 | A | * | 5/1982 | Weiss | 73/146 |
| 4,365,514 | A | * | 12/1982 | Ho | 73/592 |
| 4,372,366 | A | * | 2/1983 | Dugger | 157/13 |
| 4,516,068 | A | * | 5/1985 | Hawkinson et al. | 324/558 |
| 4,520,307 | A | * | 5/1985 | Weiss et al. | 324/558 |
| 6,050,136 | A | | 4/2000 | Hawkinson et al. | |
| 6,304,090 | B1 | * | 10/2001 | Weiss | 324/558 |
| 7,096,727 | B2 | * | 8/2006 | Adamson et al. | 73/146 |
| 7,302,836 | B2 | * | 12/2007 | Hattori | 73/146 |
| 7,439,928 | B2 | * | 10/2008 | Forster et al. | 343/806 |
| 2002/0011849 | A1 | | 1/2002 | Weiss | |
| 2005/0134444 | A1 | * | 6/2005 | Park et al. | 340/445 |

OTHER PUBLICATIONS

International Search Report and Written Opinion mailed Jan. 7, 2009.

* cited by examiner

*Primary Examiner* — Lisa Caputo
*Assistant Examiner* — Jermaine Jenkins
(74) *Attorney, Agent, or Firm* — Merchant & Gould P.C.

(57) ABSTRACT

A tire defect tester and a method of operation are disclosed. In one aspect, the tire defect tester includes a first electrode arranged to direct energy toward a tire, and a second electrode arranged on an opposite side of the tire from the first electrode to receive energy passing through the tire from the first electrode. The tire defect tester further includes an energy sensor electrically connected to the second electrode and a fault indicator circuit responsive to the energy sensor and configured to indicate the presence of a flaw upon energy above a threshold level being sensed at the second electrode.

18 Claims, 13 Drawing Sheets

TIRE DEFECT TESTER

CROSS REFERENCE TO RELATED APPLICATIONS

The present application claims priority to U.S. Provisional Patent Application No. 60/932,310, filed May 29, 2007, the disclosure of which is hereby incorporated by reference in its entirety.

TECHNICAL FIELD

The present disclosure relates generally to inspection of tire defects. In particular, the present disclosure relates to a tire defect inspection system.

BACKGROUND OF THE INVENTION

New tires are expensive. As a result, replacing and maintaining tires can be an economic burden for companies and individuals who manage a large fleet of vehicles or otherwise place excessive wear on their tires. Replacing tires can also be a burden for those of modest means. As a result, it is becoming increasingly important to repair damaged tires rather than replace them with new tires. Repairing a damaged tire is usually very simple and inexpensive, especially repairing simple holes or objects that become embedded in the treaded portion of the tire.

Diagnosis is the first step in repairing a damaged or flawed tire. It is necessary to ascertain if any foreign objects are embedded in the tread portion of the tire or if any cracks, fissures, or holes exist therein. If such defects are found to exist, the tire can be repaired. If the defect is not found, the tire must be replaced.

There are several existing techniques for inspecting a tire. One such technique is visual inspection. Visual inspection consists of rotating a tire on a mounting stand, while an inspector visually observes the tread portion of the tire as it passes beneath his gaze. Visual inspection of a tire tends to be slow and time consuming. More importantly, however, this method for searching for defects is, at best, unreliable. This is because some defects are so minute that they escape the detection of even a trained, experienced observer. Even these undetected defects can weaken the tire and become a hazard to vehicles operating at high rates of speed.

In an attempt to solve some of the problems inherent in visual inspection, other types of testing techniques have been devised. One such method involves over inflating a tire and either immersing the tire in a fluid or applying a fluid to the outer surface thereof. A leak of air through an orifice or fissure can be detected visually more readily by the observation of a bubbling effect, which will occur at the location of the defect. This method, however, will not detect defects other than well defined holes that pass all the way through the treaded portion of a tire.

More complex systems for detecting tire defects also exist. In one such system, the tread portion of a tire is sandwiched between a pair of electrodes across which a high voltage electrical potential is generated. With this system, if objects such as nails are embedded in the tread portion of the tire or if defects such as orifices or fissures exist, the voltage applied across the electrodes will cause arcing at the point of foreign object or defect. To inspect the complete tire, an inspection device typically rotates the tire such that the tread portion passes between the electrodes. An electronics package generally is included in conjunction with the electrodes, and can stop rotation of the tire and actuate an alarm once a defect is detected by arcing across the electrodes. Pinpointing the location of the defect is, thereby, facilitated.

However, even with existing systems, only a general location of the flaw in the tire determined. Additional information about the type of defect or number of defects in the tire or a series of tires could be helpful in repairing tires, as well as identifying a source of the flaw.

Furthermore, each of these tire inspection systems have limited capabilities and only detect the presence or absence of certain types of defects. These inspection systems cannot detect any characteristics or the nature of the flaw itself. Nor can the systems record related statistical information.

SUMMARY

In accordance with the following disclosure, the above and other problems are addressed by the following:

In a first aspect, a tire defect tester is disclosed. The tire defect tester includes a first electrode arranged to direct energy toward a tire, and a second electrode arranged on an opposite side of the tire from the first electrode to receive energy passing through the tire from the first electrode. The tire defect tester further includes an energy sensor electrically connected to the second electrode and a fault indicator circuit responsive to the energy sensor and configured to indicate the presence of a flaw upon energy above a threshold level being sensed at the second electrode.

In a second aspect, a method of testing tires for defects is disclosed. The method includes directing an energy signal toward a first location on a surface of a tire. The method further includes detecting an attenuated energy signal on a surface of the tire opposite the first surface. The method also includes comparing the attenuated energy signal to a predetermined energy signal value to determine the presence of a flaw in a tire at the first location.

In a third aspect, a tire tester is disclosed. The tire tester includes means for directing an energy signal toward a first location on a surface of a tire, and means for detecting an attenuated energy signal on a surface of the tire opposite the first surface. The tire tester also includes means for comparing the attenuated energy signal to a predetermined energy signal value to determine the presence of a flaw in a tire at the first location.

In a fourth aspect, a control circuit for a tire defect tester having first and second electrodes on opposite sides of a tire is disclosed. The control circuit includes a pulse generator arranged to trigger a voltage pulse at a circuit output, the circuit output electrically connectable to a first electrode. The control circuit further includes an energy sensor arranged to receive energy from a circuit input, the circuit input electrically connectable to a second electrode. The control circuit also includes a fault indicator circuit responsive to the energy sensor and configured to indicate the presence of a flaw upon energy above a threshold level being sensed at the circuit input.

In a fifth aspect, a method of detecting defects in tires using a tire tester having a control circuit is disclosed. The method includes generating an energy signal in a control circuit. The method includes detecting an attenuated energy signal, and comparing the attenuated energy signal to a predetermined energy signal value to determine the presence of a flaw in a tire.

DETAILED DESCRIPTION

Various embodiments will be described in detail with reference to the drawings. Reference to various embodiments does not limit the scope of the claims attached hereto. Additionally, any examples set forth in this specification are not intended to be limiting and merely set forth some of the many possible embodiments for the appended claims.

In general, the present disclosure relates to a tire defect tester, and controller systems incorporated into such a tire defect tester. Through use of the tire defect tester of the present disclosure, tire defects and other characteristics can be detected either automatically or manually, with improved precision. The various systems described herein can improve reliability and repeatability of tire defect detection.

Figure 1:
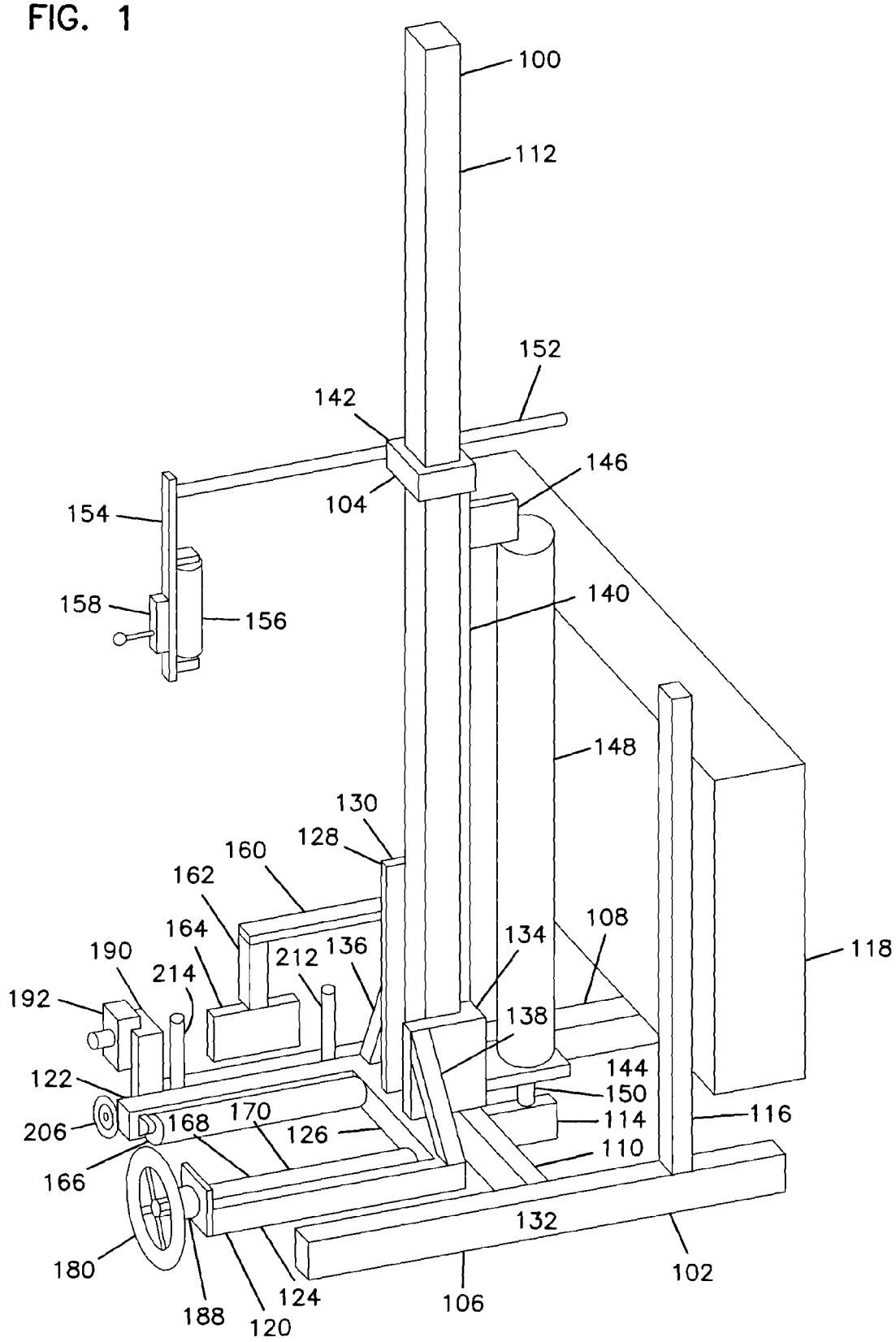
FIG. 1 is a top perspective view of a tire defect tester useable to implement aspects of the present disclosure.

Referring now to FIGS. 1-4, an example tire defect tester 10 is illustrated, in which aspects of the present disclosure can be implemented. As shown in FIG. 1, the tire defect tester 10 has a tire lift 100. One possible embodiment of the tire lift 100 has a main frame 102 and a subframe 104. The main frame 102 has two parallel base members 106 and 108 that are connected by an intermediate member 110. The intermediate member 110 is perpendicular to the base members 106 and 108. A vertical support beam 112 projects upwardly from the intermediate member 110. The vertical support beam 112 has a height sufficient that the subframe 104, and hence the tire being tested, can be raised to eye level for easy inspection. A flange 114 projects rearward from the intermediate member 110.

Two control panel supports 116 and (not shown) project upward from each of the base members 106 and 108, respectively, and a control panel 118 is mounted to the control panel supports. The control panel 118 houses a power supply and electronics for charging electrodes, which are described in more detail below in conjunction with FIGS. 5-9.

The subframe 104 slidably engages the main frame 102. The subframe 104 includes a U-shaped chassis 120 having first and second support beams 122 and 124 that are parallel to one another. An intermediate portion 126 is perpendicular to and extends between the first and second support beams 122 and 124.

A first collar 128 has three sides 130, 132 and 134. First and second sides 130 and 132 are positioned on opposite sides of the vertical support beam 112 and are attached to the intermediate member 126 of the subframe 104. The first side 130 is taller than the second side 132. The third side 134 extends between the first and second sides 132 and 134. The third side 134 is on an opposite side of the vertical support beam 112 from the intermediate member 126 of the U-shaped chassis 120. In this configuration, the first collar 128 holds the U-shaped chassis 120 to the vertical support frame 112. In order to add structural rigidity, angular reinforcement beams 136 and 138 extend between the first and second sides 130 and 132 of the collar 128 and the intermediate portion 126 of the U-shaped chassis 120.

A vertical subframe beam 140 extends upward from the third side 134 of the first collar 128 and is positioned proximal to a rear surface of the vertical support beam 112 of the main frame 102. A second collar 142 is mounted around the vertical support beam 112 of the main frame 102 and is attached to the vertical subframe beam 140.

A first cylinder flange 144 extends rearward form the third side 134 of the first collar 128. A second cylinder flange 146 extends rearward from the vertical subframe beam 140 and is proximal to the second collar 142. A hydraulic cylinder 148 is vertically oriented and extends between the first and second cylinder flanges 144 and 146. The hydraulic cylinder 148 has a cylinder arm 150 that projects downward and passes through the first cylinder flange 144. The cylinder arm 150 is attached to the flange 114 of the main frame 102.

A horizontally oriented bar 152 is attached to the second collar 142, and has a bracket 154 extending downward from one end. A vertical stabilization roller 156 is mounted to the bracket 154 and faces rearward toward the vertical support beam 112 of the main frame 102. The bar 152 slidably engages the second collar 142 so that the position of the vertical stabilization roller 156 is adjustable.

A hydraulic valve 158 is mounted on the front of the bracket 154 and is connect to the hydraulic cylinder 148 via hoses (not shown). An operator can actuate the valve 158 to cause the cylinder arm 150 to either retract into or extend from the hydraulic cylinder 148. Causing the cylinder arm 150 to extend from the hydraulic cylinder 148 will cause the first and second collars 128 and 142 to slide along the vertical support beam 112 of the main frame 102, and thus the subframe 104 to move upward. Likewise, causing the cylinder arm 150 to retract will cause the subframe 104 to move downward relative to the main frame 102. In order to aid movement of the subframe 104, bushings or bearings can be placed between the first and second collars 128 and 142 and the vertical support beam 112.

An electrode bracket 160 is pivotally connected to the first side 130 of the first collar 128, and is positioned toward the top edge of the first side 130. An insulating bracket 162 is detachably connected to the projecting end of the electrode bracket 160, and a first electrode 164 is mounted to the insulating bracket 162. The first electrode 164 is electrically connected to the control panel 118 with wires (not shown). The first electrode 164 is described in more detail below. An advantage of pivotally mounting the electrode bracket 160 is that the position of the first electrode 164 can be adjusted slightly to ensure good contact with the inner surface of a tire's tread portion. Additionally, an interlock (not shown) can be operatively connected between the first electrode 164 and the electrode bracket 160. The interlock would prevent the first electrode 164 from being energized when not properly attached to the electrode bracket 160.

First and second drive rollers 166 and 168 are mounted to the first and second support beams 122 and 124, respectively, of the U-shaped chassis 120 with bearing assemblies 169 and (not shown). The first roller 166 is made from an insulating material such as rubber. Rubber is advantageous because it provides traction with a tire. The second roller 168 has ribs extending along its length to provide traction with a tire that is mounted in the tire lift. Additionally, the second roller 168 is formed from a metallic roller to form a second electrode 170. The second roller 168 is then electrically connected to the circuitry in the control panel 118 and is grounded. This distance is advantageous because the tread portion of a tire can rest on the first and second rollers 166 and 168.

Figure 2:
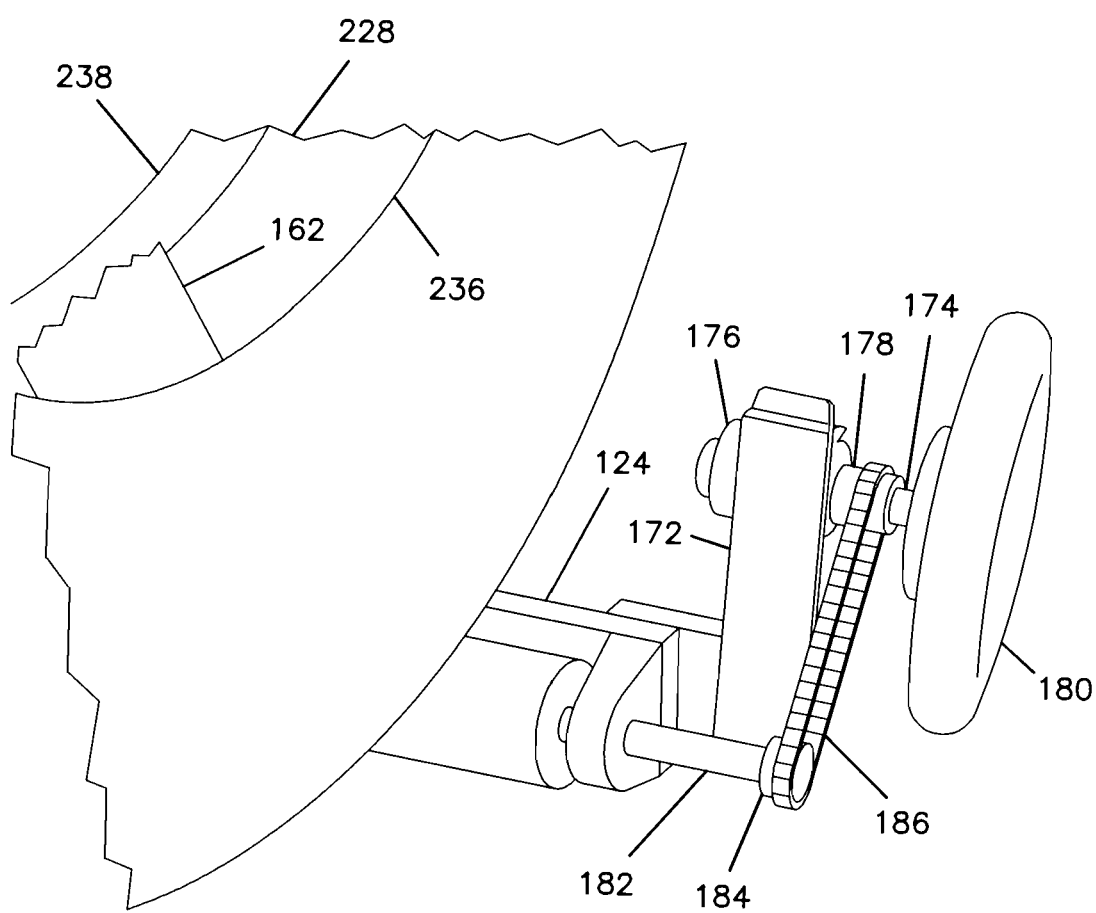
FIG. 2 is a fragmentary view illustrating a drive roller and crank assembly shown in FIG. 1.

Referring to FIGS. 1 and 2, a bracket 172 is mounted on the end of the second support beam 124 of the U-shaped chassis 120. A spindle 174 is mounted to the bracket 172 by a bearing assembly 176. A first sprocket 178 and a first hand wheel 180 are mounted on the spindle 174. In turn, the second drive roller 168 has an axle 182 that extends outward from one end. A second sprocket 184 is mounted on the axle 182 of the second drive roller 168. A chain 186 extends around the first and second sprockets 178 and 184. Additionally, a cowling 188 (not shown in FIG. 2) provides protective covering for the chain 186, the first sprocket 178, and the second sprocket 184.

In an alternative embodiment, a motor (not shown) is mounted to the subframe 104 in place of the first hand wheel 180. The motor would permit automatic rotation of the second drive roller 168, and hence automatic rotation of the tire.

Figure 3:
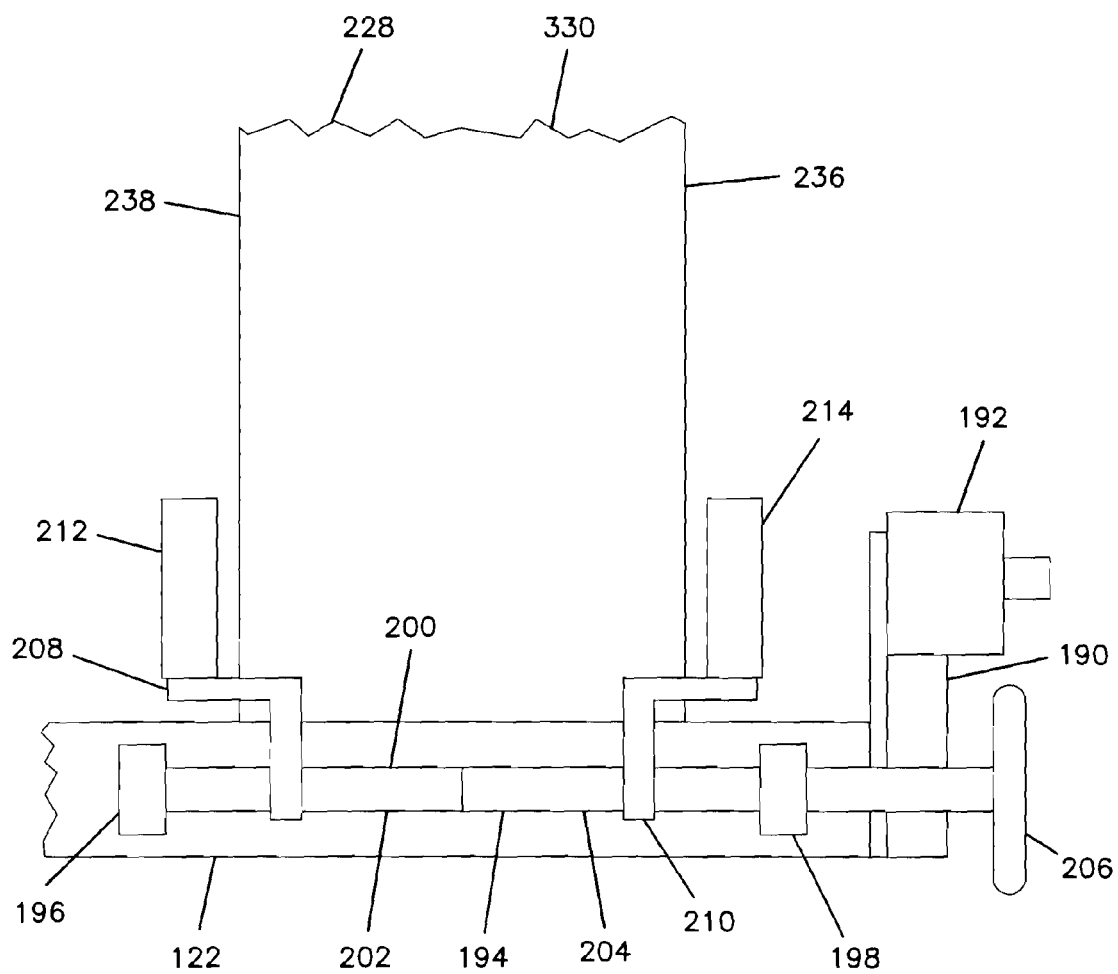
FIG. 3 is a fragmentary view illustrating a roller assembly shown in FIG. 1.

Referring to FIGS. 1 and 3, a bracket 190 is mounted on the end of the first support beam 122 of the U-shaped chassis 120 and an electrical switch 192 is mounted on the bracket 190. The electrical switch is connected to the power supply and circuitry in the control panel via wires (not shown). Actuating the electrical switch 192 will energize the first and second electrodes 164 and 170.

A screw mechanism 194 is also rotatably mounted to the first support beam 122 of the U-shaped chassis 120 by first and second bearing assemblies 196 and 198. The screw mechanism 194 has a treaded rod 200 that has first and second portions 202 and 204. The first portion 202 has threads in one direction, and the second portion 204 has threads in an opposite direction. A second hand wheel 206 is mounted on the end of the threaded rod 200.

A first roller bracket 208 is mounted to the first portion 202 of the treaded rod 200, and a second roller bracket 210 is mounted to the second portion 204 of the thread rod 200. First and second rollers 212 and 214 are mounted to the first and second brackets 208 and 210, respectively, and are then horizontally spaced. The first and second rollers 212 and 214 are arranged and configured to be positioned proximal to the sidewalls of a tire. The distance between the first and second rollers 212 and 214 is adjustable by turning the second hand wheel 206. Turning the second hand wheel 206 in one direction will cause the first and second rollers 212 and 214 to move closer together, and turning the second hand wheel 206 in an opposite direction will cause the first and second rollers 212 and 214 to move farther apart.

Figure 4:
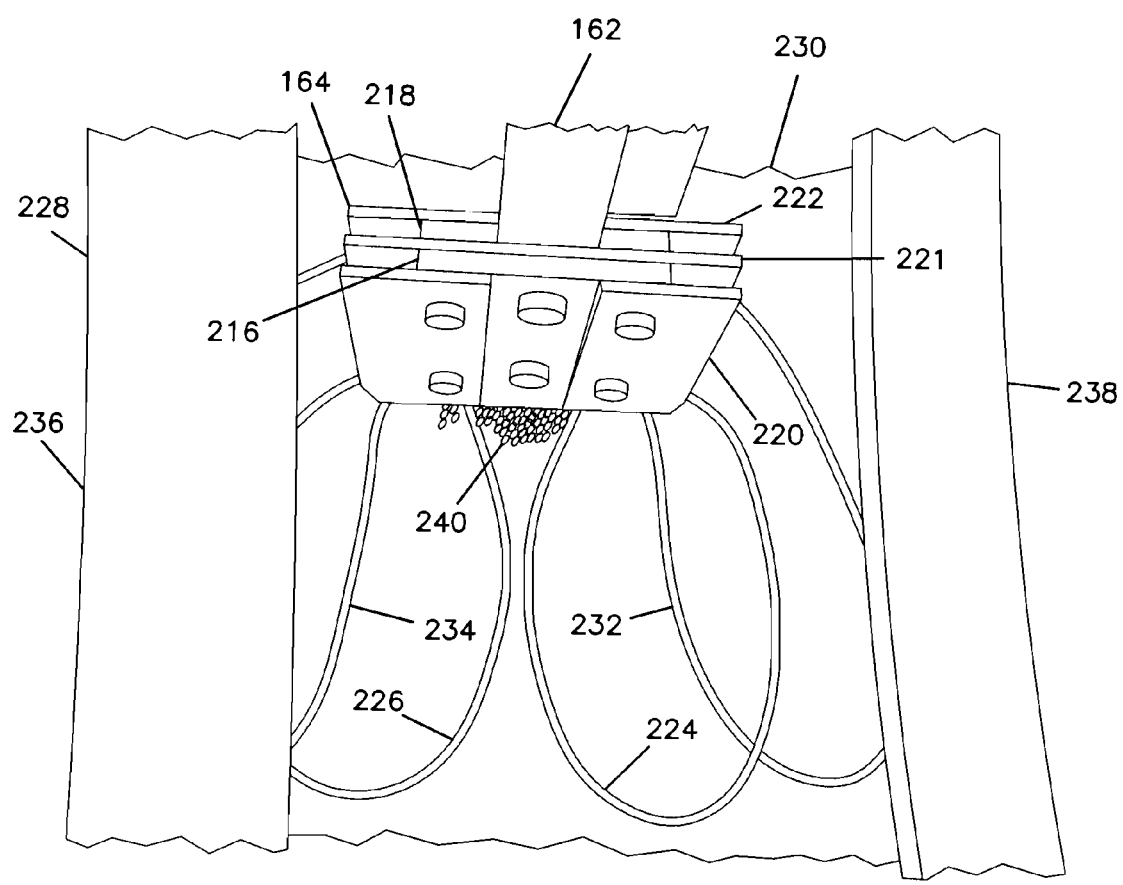
FIG. 4 is a fragmentary view illustrating a first electrode assembly shown in FIG. 1.

Referring now to FIG. 4, the first electrode 164 has two conductive plates 216 and 218 that are isolated by insulators 220 and 222 and are mounted to the insulating bracket 162. A first pair of wire lobes 224 and 226 are in electrical communication with the first conductive plate 216. The first pair of wire lobes 224 and 226 project downward so that they engage the inner surface of the tire's 228 tread portion 230. A second pair of wire lobes 232 and 234 are in electrical communication with the second conductive plate 218 and project from opposite sides of the electrode 162. In this configuration, the second pair of wire lobes 232 and 234 engage the region between the tire's tread portion 230 and sidewalls 236 and 238.

Additionally, a series of beaded chains 240 hang downwardly from the electrode 164. The first pair of lobed wires 224 and 226, the second pair of lobed wires 132 and 134, and the beaded chains 240 are all electrified when the first electrode 164 is energized. One type of electrode that can be used is model no. INTER-NDT-LT (called Probe—for Light Truck), which is manufactured by the Paul E. Hawkinson Company, having its principal place of business in Minneapolis, Minn.

Other example tire defect testers may be used as well, in accordance with the present disclosure. Example tire defect testers, and systems for detecting flaws in tires, are shown in U.S. Pat. Nos. 6,050,136, filed Apr. 16, 1998, and 4,516,068, filed Apr. 16, 1983. The disclosures of each of these patents are hereby incorporated by reference in their entireties.

In use, an operator will lower the subframe 104 so that the U-shaped chassis 120 is proximal to the base members 106 and 108 of the main frame 102. The worker then removes the first electrode 164 and insulating bracket 162 from the electrode bracket 160 to clear room for a tire. The operator rolls a tire onto the U-shaped chassis 120 so that the tread portion 330 of the tire 228 rests on the first and second drive rollers 166 and 168.

In this position, the stabilization roller 156 is proximal to the outer sidewall 236 of the tire 228. The operator can adjust the position of the stabilization roller 156 by sliding the bar 152 relative to the second collar 142. Additionally, the tire 228 is positioned between the first and second horizontally spaced rollers 212 and 214. The operator can then rotate the second hand wheel 206 and adjust the distance between the first and second horizontally spaced rollers 212 and 214. The stabilization roller 156, as well as the first and second horizontally spaced rollers 212 and 214 should be proximal to the sidewalls 236 and 236 of the tire 228, but not necessarily touching the tire 228.

In this configuration, the rollers 152, 212, and 214 stabilize the tire 228 while it is rotating, as described below. Stabilizing the tire 228 is important because the tire 228 may wobble because of conditions such as uneven wear in the treads or because of the narrow width of the tire 228 relative to its height. Because most tires have similar sizes, the operator typically does not need to adjust the rollers 156, 212 and 214 prior to testing each tire. An adjustment needs to be made only if there is a relatively drastic change in the size of tires being tested.

After the tire 228 is mounted, the operator will actuate the hydraulic valve 158 and cause the cylinder arm 150 to extend, thereby raising the tire 228. The operator typically raises the tire 228 to a level where he/she can easily peer into the tire 228 or observe the outer surface of the tread portion 230 proximal to the second drive roller 168. The operator then positions the first electrode 164 in the tire 228 and attaches the insulating bracket 162 to the electrode bracket 160. In this position, the interlock will permit the electrodes 164 and 170 to be energized. An alternative embodiment includes a mirror (not shown) operably connected to the subframe 104 and positioned so that the operator can observe arching from the second electrode 170 without bending over.

Once the first electrode 164 is in place, the operator can actuate the switch 192 and energize the first and second electrodes 164 and 170. The operator turn the first hand wheel 180 to rotate the tire 228, which moves the inner surface of the tread portion 230 against the first electrode 164 and the outer portion of the tread portion 230 against the second electrode 170. The operator watches for arcing that occurs from either one of the electrodes 164 or 170. The operator can also listen for arcing, which will make a popping or cracking noise.

When an arc occurs, the operator will stop rotating the tire 228 and release the switch 192, which causes the electrodes 164 and 170 to deenergize. The operator can then safely mark the location of the defect for repair. After marking the operator reenergizes the electrodes 164 and 170 and continues to rotate the tire 228.

This process is continued until the entire tire 228 has been inspected. The operator then lowers the subframe 104, detaches the first electrode 164, and rolls the tire 228 off the tire lift 100.

In further embodiments, particularly with respect to those embodiments of the tire tester incorporating the circuitry described below, circuitry is provided in conjunction with the tire tester which operates a motor and generates pulses to be applied across the electrodes. Details regarding such embodiments are described below, in conjunction with FIGS. 5-13.

Referring to FIGS. 5-13, various possible embodiments of electrical systems and controllers are shown that can be used in the tire defect detector arrangements of FIGS. 1-4, as well as with other configurations of tire defect testers, including other embodiments of structures for electrodes, mounting a tire, supporting a tire, and rotating a tire to an electrode arrangement.

Figure 5:
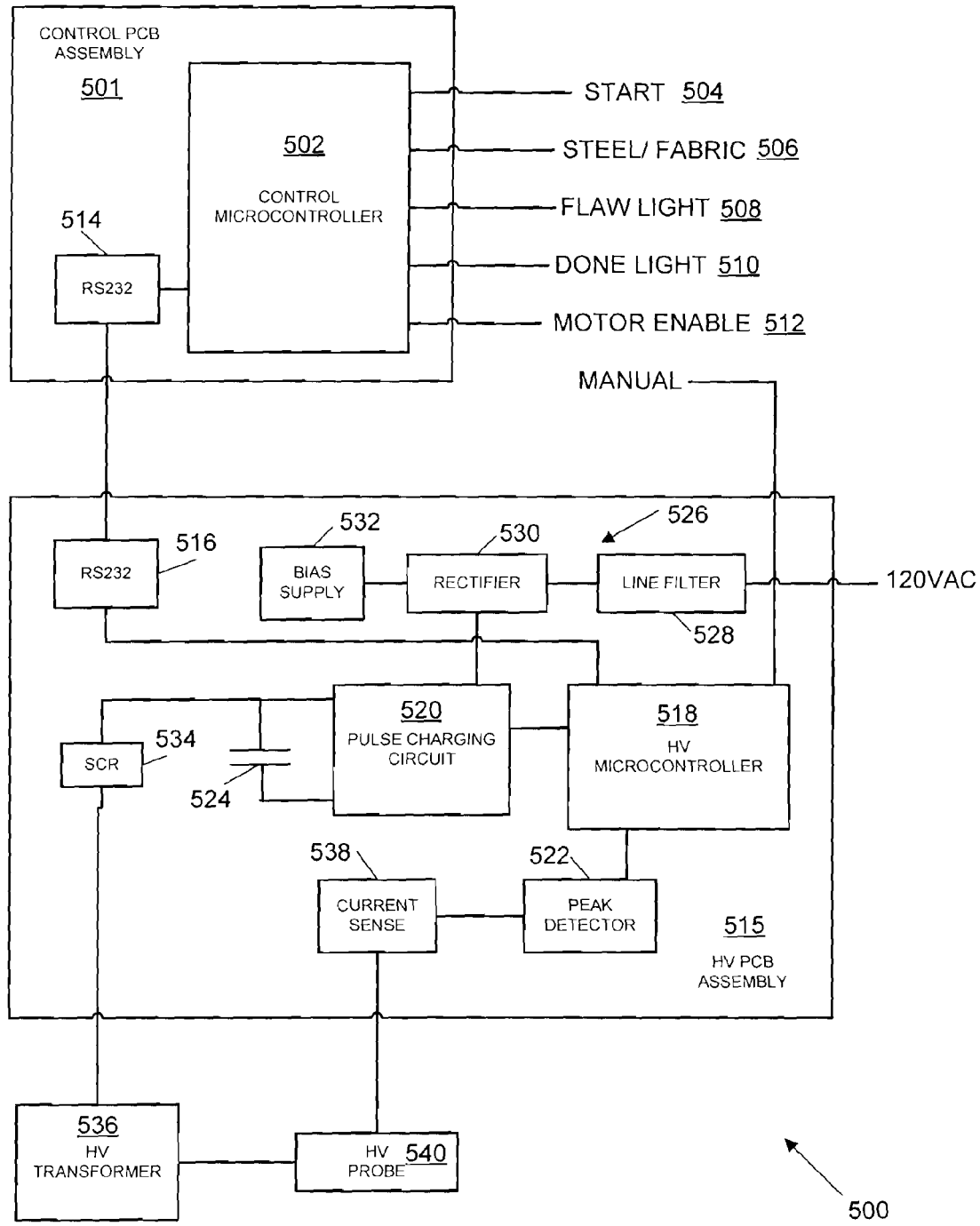
FIG. 5 is a schematic block diagram of a controller system useable in a tire defect tester, according to a possible embodiment of the present disclosure.

FIG. 5 illustrates a schematic block diagram of a controller system 500 useable in a tire defect tester, according to one possible embodiment of the present disclosure. Generally, the controller system 500 provides electrical control and operation in a tire defect tester. The controller system 500 can be used in any of a variety of types of tire defect testers; one example is the tire defect tester 10 discussed above.

In the embodiment shown, the controller system 500 includes a control assembly 501 which includes a control microcontroller 502 interfaced to a number of input and output signals, including a start switch 504, a tire type indicator 506, a flaw indicator 508, a completion indicator 510, and a motor enable output 512. The control microcontroller 502 also is configured to send and receive data via an RS-232 port 514. The tire type indicator 506 provides an indication corresponding to the type of tire being tested (e.g. steel belted or fabric tire). The type of tire tested affects the energy applied across the tire during testing—steel belted tires require less energy due to the conductor within the tire. The flaw indicator 508 provides an indication (e.g. sound or light) indicating the existence of a flaw in the tire. The completion indicator 510 provides an indication (sound or light) indicating that the testing of that tire has completed. These indicators can correspond to LED or other displays, buzzers, or other perceptible user notifications.

In the embodiment shown, the controller system 500 includes a high voltage assembly 515 which is interfaced to the control assembly by connection of a complementary RS-232 port 516 to the RS-232 port 514 of the control assembly. The RS-232 port 516 provides a data input/output interface for a microcontroller 518 in the high voltage assembly, which is in turn interfaced to a pulse charging circuit 520 and a peak detector 522.

The pulse charging circuit 520 is connected in parallel with a capacitor 524 and is used in conjunction with the microcontroller 518 to power the capacitor 524. The pulse charging circuit 520 receives power from a power conditioning circuit 526, which, in the embodiment shown, includes a line filter 528 interconnected to a 120 VAC input power supply, a rectifier 530 (to which the pulse charging circuit 520 is directly connected), and a bias supply 532. The pulse charging circuit 520 interconnects to a Silicon-Controlled Rectifier (SCR) 534, which selectively discharges the capacitor 524 when the pulse charging circuit 520 is deactivated, to provide a voltage to a transformer 536 interconnected to the SCR 534 (from the discharging capacitor).

The high voltage probe 540 is powered via the transformer 536, and pulses based on the discharge from the capacitor 524. The pulses from the high voltage probe 540 pass through a tire under examination, to a current sensing module 538. The current sensing module 538 detects current at an output of a high voltage probe 540. The peak detector 522, which is electrically connected to the current sensing module 538, detects peak energy received at the current sensing module 538.

In alternative embodiments of the controller system 500, other communicative connections can be used in place of the RS-232 ports 514, 516, such as other parallel or serial data connections using synchronous or asynchronous communication protocols. Furthermore, microcontrollers 502, 518 can be replaced by microprocessors or other types of programmable circuits. Additional inputs to the controller system 500 are possible as well.

In use, an operator initiates operation of the control system 500 by pushing the start switch 504. After a short delay, the motor starts (e.g. by activating the motor enable output 512) and the control microcontroller sends a command to the high voltage assembly 515 via the RS-232 connection (interconnected RS-232 ports 514, 516) to initiate the microcontroller 518 to trigger a high-voltage pulse. This command includes a setting for the peak detector A/D on the high voltage assembly 515 and a bit to indicate the steel/fabric setting (e.g. as indicated by the tire type indicator 506), which can alter the energy supplied to the high voltage probe 540.

When the high voltage assembly 515 receives the command, the microcontroller 518 starts the pulse charging circuit 520. This circuit charges capacitor 524 to a level determined by the setting of the steel/fabric indicator 506. For example, the circuit can direct a lesser charge onto the capacitor in the case of a steel-belted tire than in the case of a fabric tire, to prevent false arcing when a steel tire is tested. Since the energy in a capacitor is proportional to the square of the voltage on the terminals of the electrodes of the system, charging and discharging the capacitor supplies a fixed amount of energy to the electrode (i.e. part of the high voltage probe 540). About 20 milliseconds after starting the charge, the microcontroller 518 stops the charging circuit 520 and triggers the SCR 534, discharging the capacitor 524 through the primary of the transformer 536. In the embodiment shown, the transformer 536 has a turn ratio of about 121:1, so a capacitor (e.g. capacitor 524) charged to about 200 volts will create a high-voltage pulse of about 24,200 volts on the high voltage probe 540.

If a flaw is present on the tire, the insulation provided by the tire between the high voltage probe 540 and ground (e.g. shown in FIG. 6) will break down and current will flow in the secondary winding of the transformer 536. The current sensor 538 on the high voltage assembly 515 measures this energy as compared to the threshold set previously by the command received from the control microcontroller 502.

The result, in the form of a byte indicating the existence or absence of a flaw, is passed back to the control microcontroller 502. If the result was a flaw, the control microcontroller 502 stops the motor and illuminates the flaw light (e.g. by activating the flaw indicator 508). If the result was no flaw, the control microcontroller 502 can send another command to the microcontroller 518 and initiates another high-voltage pulse.

In certain embodiments, the system 500 has a selectable manual mode. In the manual mode, a user closes a manual switch, which starts the motor and causes the high voltage microcontroller 518 to generate high-voltage pulses at a repeated rate (e.g. about a 20 ms rate). This manual mode is used to enable the operator to manually locate the actual flaw on a tire.

In further embodiments, the controller system includes a set up adjustment, which corresponds to the threshold of the peak detector to determine a flaw or no flaw condition. This adjustment occurs on the control assembly 501. It is converted to a digital byte and transmitted to the high voltage assembly 515 alongside the command passed between the RS-232 interfaces 514, 516.

Through use of certain embodiments of the system 500, various aspects of every high voltage pulse applied to the tire are controlled. In at least some embodiments, pulse timing, energy level, and flaw detection threshold are all established by software executed on the control microcontroller 502 and microcontroller 518 of the high voltage assembly. For example, the control microcontroller 502 can accomplish pulse timing control by triggering each high voltage pulse of the high voltage probe 540 separately, on a programmable, periodic basis. Similarly, the energy level of the pulse can be dictated by the control microcontroller 502 and the high voltage assembly microcontroller 518, by transmitting an expected charge value and triggering a high voltage probe pulse when an appropriate voltage is reached on the charging capacitor 524. Likewise, the microcontrollers 502, 518 can establish a value for the flaw detection threshold corresponding to the total energy detected, such that a different threshold (e.g. expected energy observed) is associated with each pulse. In such embodiments, each pulse is generated independent of all other pulses, and the results of each pulse are independently detected and evaluated before another is generated. This arrangement allows the system 500 to stop on the same pulse in which a flaw is detected. This allows the system to react more quickly to detection of a flaw, thereby more accurately indicating the location of the flaw in the tire by halting the tire rotation at the location of the flaw.

In certain further embodiments (in particular embodiments employing the high voltage assembly of FIGS. 9-13, below), each pulse is generated separately. In these embodiments, each pulse can be assigned a unique energy level, or differing timing or detection levels. By varying energy levels, timing, and detection levels, it may be possible to further profile, measure, or grade detected flaws in tires related to type, severity, and size. For example, a tire tester can obtain a more accurate flaw profile across a tire by increasing the pulse frequency of the high voltage probe; also, the amount of energy by which the pulse exceeds a threshold energy might indicate the severity or type of a flaw. Furthermore, a large number of flaw indications in succession, or a flaw indication at even low energy levels may correspond to a large flaw present in a tire.

Figure 6:
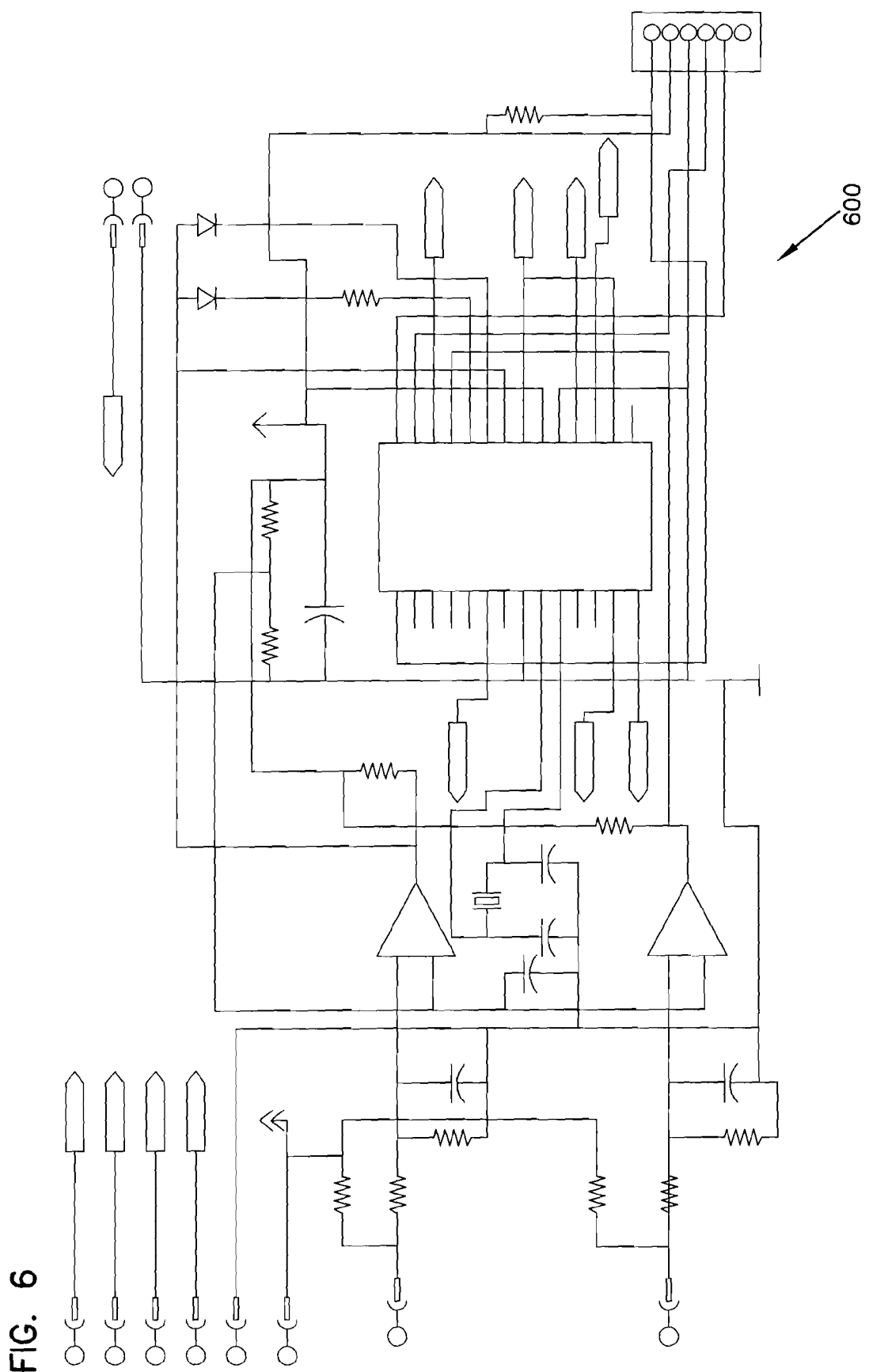
FIG. 6 is a schematic view of aspects of a controller system useable in a tire defect tester, according to a possible embodiment of the present disclosure.
Figure 7:
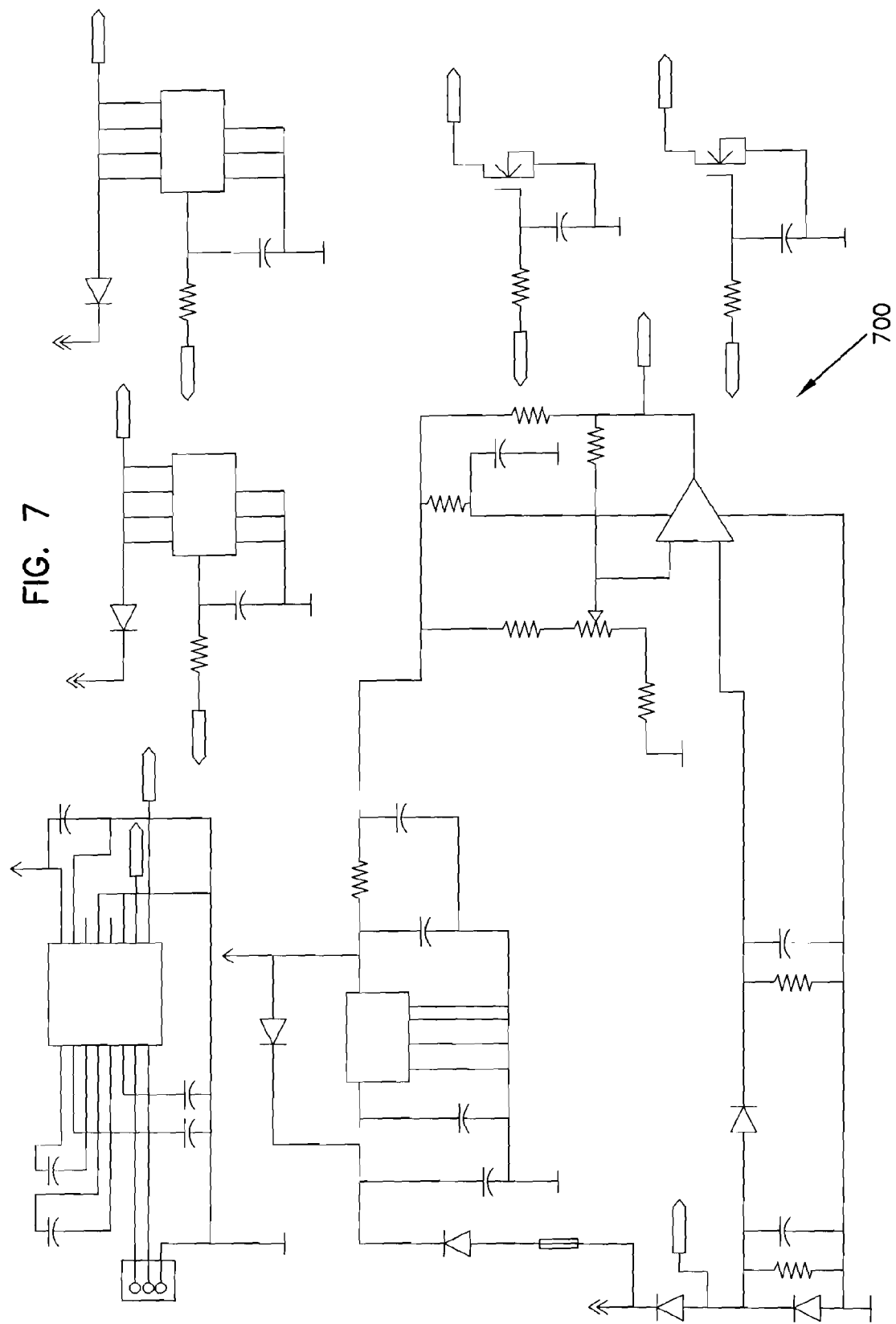
FIG. 7 is a further schematic view of aspects of a controller system useable in a tire defect tester, according to a possible embodiment of the present disclosure.
Figure 8:
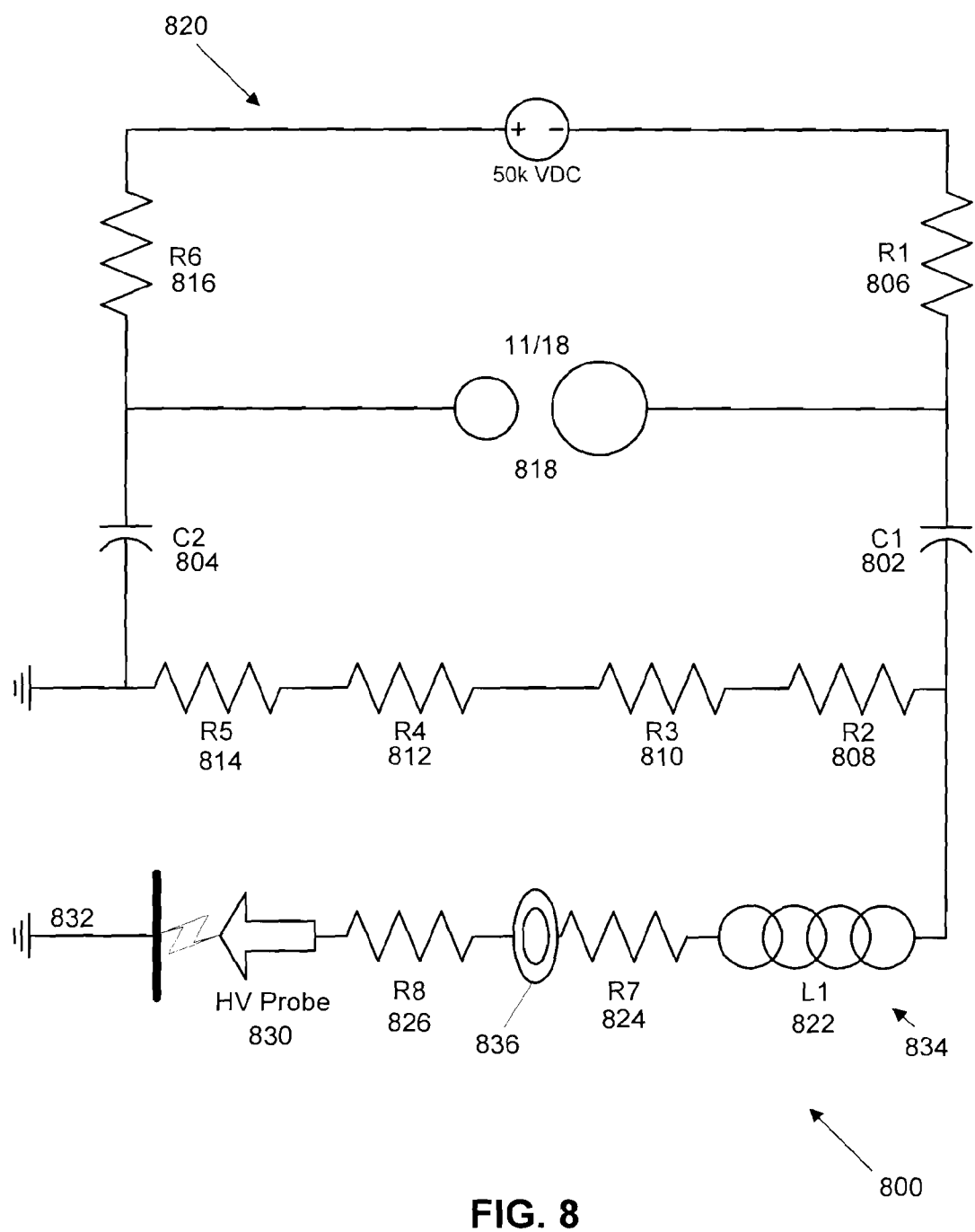
FIG. 8 is a schematic view of electrical systems useable in a tire defect tester, according to a possible embodiment of the present disclosure.

Now referring to FIGS. 6, 7, and 8, schematics of circuitry useable in a tire defect tester, according to certain possible embodiments of the present disclosure. FIG. 6 illustrates details of one of many possible embodiments of a control block portion 600, which provides details of certain aspects of the control assembly 501 of FIG. 5. FIG. 7 illustrates details of one of many possible embodiments of a further control block portion 700, such as can be used in conjunction with the portion 600 to form a control circuit. The control circuit, formed from portions 600, 700, generally sends commands to a high voltage circuit for activation/deactivation of the flaw detection tester, which in turn generates electrical signals used to periodically activate a high voltage probe to detect flaws in tires.

When used with the embodiment of the high voltage circuit of FIG. 8, below, a current transformer (e.g. current transformer 836 in the circuit 800 of FIG. 8) is connected to pin X2-2 on the control block 700. An approximately 10 ohm resistor (R1, shown in FIG. 8) provides the termination for the current transformer and converts the current wave form from a high voltage probe (e.g. high voltage probe 830) to a voltage waveform. This voltage waveform is peak detected by diode U3 and C2, seen in FIG. 7. R2 provides a long decay time constant for the voltage on C2. Because the current in the circuit portion 700 is determined by the energy level in the current sensor of the high voltage assembly 515, the voltage on C2 of FIG. 7 at the conclusion of the high voltage pulse reflects that energy level. Therefore, the discharge time of C2 R2 will also reflect the energy level and the presence of a flaw. Comparator U5 converts the saw-toothed waveform on C2 to a pulse, the width of which represents the amount of energy that passed through the high voltage probe during the last high voltage pulse. Micro controller IC2 then measures the width of this pulse and decides whether the pulse represents a flaw.

In operation, an operator starts the test sequence by pushing the Start button, connected to X1-3. This signals the microcontroller IC2 (of FIG. 6) to turn off the flaw light and turn on the motor and the high voltage signal. The high voltage circuit (seen in FIG. 7) then cycles (or is pulsed), producing a high voltage spike periodically (in the case of the circuit of FIG. 8, every 20 ms on the high voltage probe 830). Each pulse produces a signal to the microcontroller from the peak detector, seen as U7 of FIG. 8, and comparator U5. If one of the pulses from the comparator circuit exceed the threshold time, which is typically about 2 ms, the microcontroller turns off the motor and high voltage and turns on the flaw light, stopping the tire with the probe resting on the flaw.

In the embodiment shown, a 20 turn potentiometer Q3 is used to adjust sensitivity of the detector circuit. The potentiometer Q3 adjusts the comparator threshold and adjusts the length of the pulse from the comparator U5. The operator sets the potentiometer Q3 such that the system 700 trips only on flaws. In further embodiments, the sensitivity of the detector circuit can be set in different ways. For example, the sensitivity of the detector circuit can be set by a microcontroller integrated in the system, and can be programmable.

Now referring to FIG. 8, an embodiment of an electrical system 800 is shown that is useable in a tire defect tester. The electrical system 800 can be used, in certain embodiments, within the system 500 above, to provide a probe circuit driven either manually or by a control circuit. In such embodiments, the electrical system 800 generally provides the functionality of the high voltage assembly 515 of FIG. 5, as well as the high voltage probe 540 and high voltage transformer 536. In the embodiment shown, the electrical system 800 includes a pair of capacitors C1802 and C2 804 that, along with a set of six resistors R1 806, R2 808, R3 810, R4 812, R5 814, and R6 816, as well as a spark gap 818, forms a relaxation oscillator 820. The relaxation oscillator 820 portion of the electrical system 800 generates a saw-tooth wave in which the capacitors C1802 and C2 804 are cyclically charged and discharged.

Although in various embodiments, the resistors may differ in value, in the embodiment shown, R1 806 has a value of about 20 MOhms, R2 808 has a value of about 75 Ohms, R3

810 has a value of about 75 Ohms, R4 812 has a value of about 5 kOhms, R5 814 has a value of about 5 kOhms, and R6 816 has a value of about 1MOhm. Furthermore, the capacitors C1-C2 802, 804 as shown can each have values of about 0.001 uf. These values may differ in alternative embodiments of the present disclosure.

In an example embodiment, the series combination of C1 802 and C2 804 charge to about 50 KV (about 25 KV each) through the resistor chain 806-816. When the voltage across the spark gap 818 reaches about 50 KV, the air in the spark gap ionizes into conductive plasma, shorting the two capacitors C1 and C2 together. The capacitors C1 802 and C2 804 then discharge through R2, R3, R4, and R5 (808-814) producing a high voltage pulse on the right terminal of L1 822. In the embodiment shown, this sequence repeats at about a 20 ms rep rate.

L1 822, along with R7 824, R8 826, and the stray capacitance between a high voltage probe 830 and ground 832 form a tuned LRC circuit 834. When the spark discharges C1 802 and C2 804, a short 50 KV pulse appears at the right terminal of L1 822. This causes the LRC circuit 834 to produce its natural impulse response, which can be observed on the output of a current transformer 836.

In the embodiment shown, L1 has a value of about 1 MH, and the resistors R7 824 and R8 826 each have resistance values of about 150 Ohms. These values may also vary in different embodiments of the present disclosure.

The presence of a flaw in the tire changes the circuit at the point of the high voltage probe 830. The exact nature of the flaw will determine the nature of the change. Generally, the change will increase the stray capacitance, decrease the stray resistance, and change the threshold voltage where a spark will occur at the high voltage probe tip or a combination of all three. In any case, the distribution of energy from C1 802 and C2 804 between the R2, R3, R4, R5 (808-814) path and the high voltage probe path is altered, with more energy passing through the high voltage probe. The circuit 800 uses this difference in energy distribution to detect flaws.

Measuring the relative energy level of each high voltage pulse through the probe and hence the energy dissipated in the high voltage probe path enables detection of a wider variety of flaws and determination of the nature of the flaw itself. It also enables recording statistical information about the flaws detected, such as a number or distribution of flaws detected on a tire or set of tires.

Referring now to FIGS. 9-13, schematics are shown for circuitry related to a high voltage assembly useable to detect flaws in tires, according to a further possible embodiment of the present disclosure. The circuit illustrated in the schematics of FIGS. 9-13 can be used as an alternative to the circuit 800 of FIG. 8 to provide a high voltage signal for detecting flaws in tires. In certain embodiments, the systems disclosed in FIGS. 9-13 correspond to the high voltage assembly 515 of FIG. 5.

Figure 9:
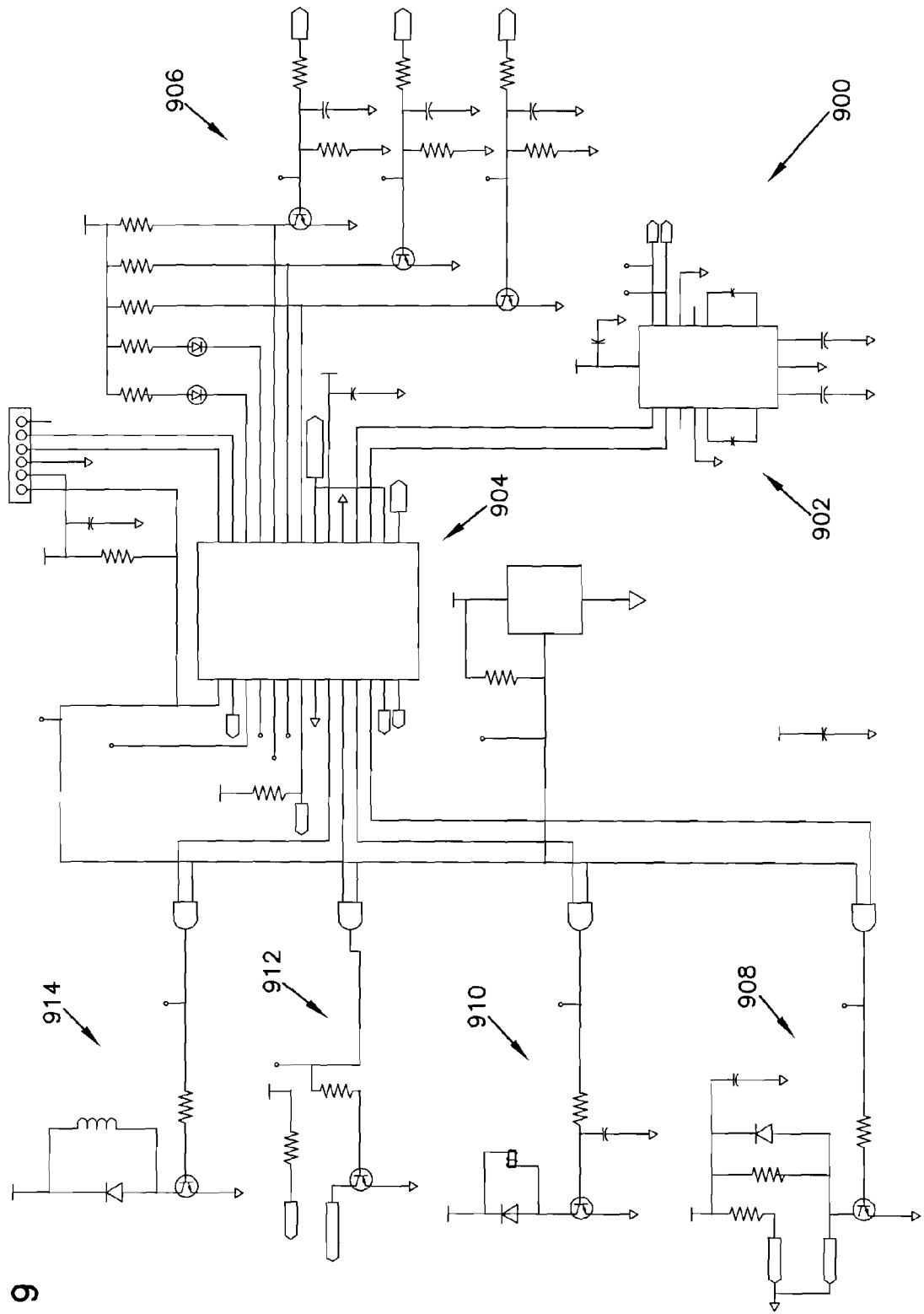
FIG. 9 is a schematic view of a high voltage assembly useable in a tire defect tester, according to a further possible embodiment of the present disclosure.

As seen in FIG. 9, the circuit portion 900 includes a communication circuit 902, a processing circuit 904, an input circuit 906, a trigger circuit 908, an AC circuit 910, a charge circuit 912, and a voltage setting circuit 914. The communication circuit 902 includes an RS-232 interface chip U12, interconnecting to data send and receive serial links, monitored at tap points TP36 and TP37, respectively. The communication circuit 902 includes capacitors C39, C40, C41, C43, C44 for managing voltage delivered to the chip.

The interface chip U12 also communicatively interconnects to the processing circuit 904 at a high voltage microcontroller U10, which in certain embodiments corresponds to high voltage microcontroller 518 of FIG. 5. The high voltage microcontroller U10 interconnects to the input circuit 906, trigger circuit 908, AC circuit 910, charge circuit 912, and voltage setting circuit 914. Also included in the processing circuit are a monitor U11, as well as discrete components R51, R61. A connector J5 allows direct connection to and programming of the high voltage microcontroller U10, and connects via resistor R41 and capacitor C33.

The input circuit 906 includes a number of input signals (e.g. that can be received from a control assembly), including a spare input, an enable input, and a manual input. These inputs are each connected to the high voltage microcontroller U10 by resistor-capacitor circuits (formed by R47, R55, and C34; R49, R56, and C38; R50, R57, and C37, respectively) as well as solid-state switches (shown as BJT-type transistors Q4, Q6, and Q7, respectively). An input voltage of about 5 VDC provides an upper signal logic level to the input signals, and interconnects to the signals via resistors R44, R45, and R48. Resistors R42 and R43 connect to diodes D16 and D17 which indicate activity of the high voltage microcontroller U10.

The trigger circuit 908 includes pulse outputs for outputting to a high voltage probe. The pulse outputs are connected to the high voltage microcontroller U10 via signal conditioning circuitry, including a solid state switch Q9, which activates the pulse outputs based on an output from microcontroller U10. Additional circuitry, including resistors R9, R53, R54, diode D20, and capacitor C49 connect the pulse outputs to a voltage of about 5 VDC or ground, respectively.

The AC circuit 910 activates alternating current from the circuit 900. The AC circuit 910 includes an AND gate U9B that, when enabled, passes a signal through R52 to the gate of a solid state switch (BJT transistor) Q6, which causes a voltage difference between a 12 VDC source and a common ground, activating a diode D19, connected in parallel with a power relay K1:A.

Figure 10:
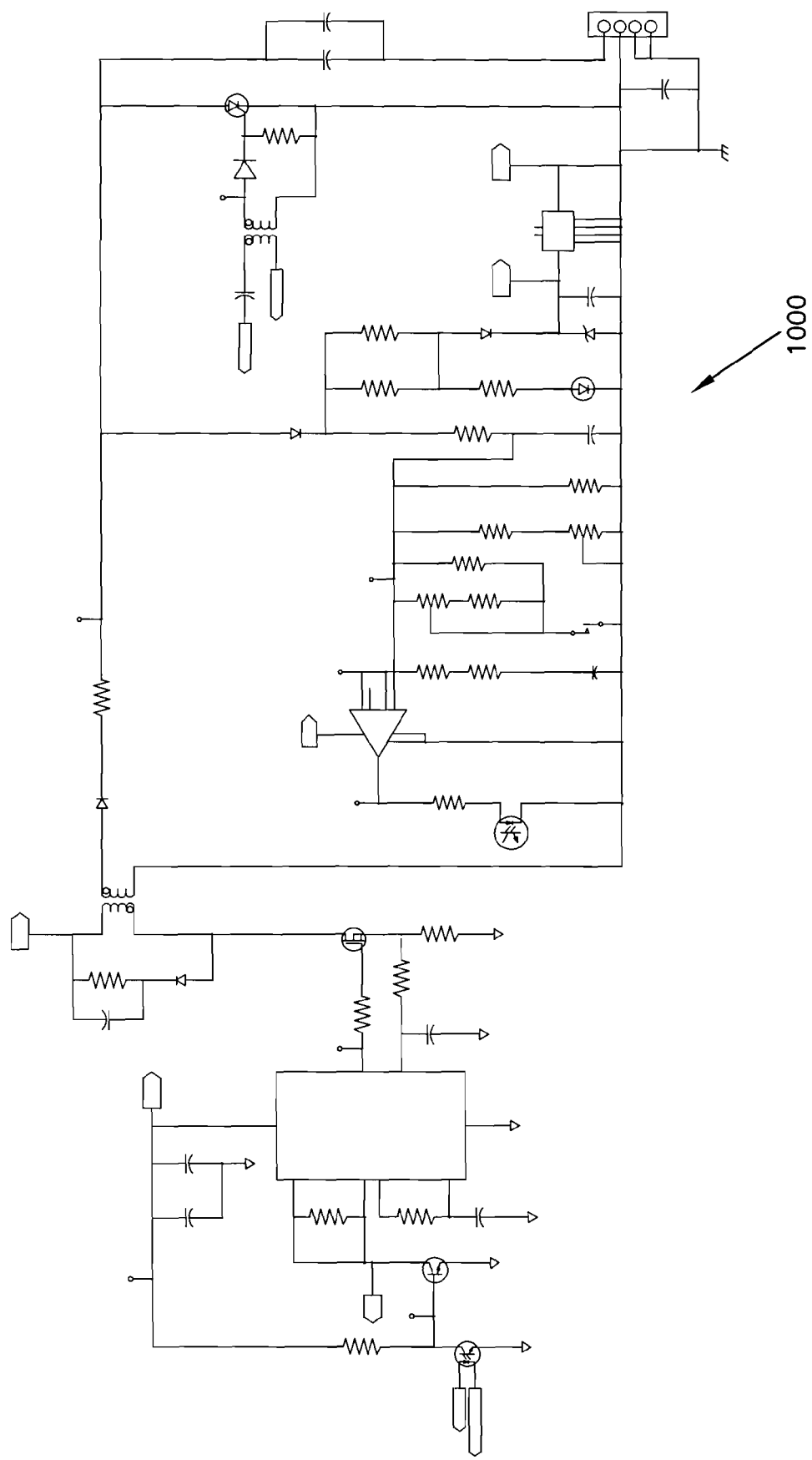
FIG. 10 is a further schematic view of a high voltage assembly useable in a tire defect tester, for use in accordance with the embodiment of FIG. 9.

The charge circuit 912 activates a capacitor charging circuit used to activate a pulse charging circuit (e.g. as seen in FIG. 10). The charge circuit 912 includes an AND gate U9C that, when enabled, activates a charge and charge return output through use of resistors R58, R59. The charge return is tied (when the circuit is activated) to a common voltage by a solid state switch Q10 (BJT transistor).

The voltage setting circuit 914 activates a voltage of about 12 VDC through a coil, as directed by a diode and switch Q5 (BJT) when activated by an AND gate U9A through resistor R48.

FIG. 10 illustrates aspects of the high voltage assembly as a circuit 1000, which includes functionality corresponding to the pulse charging circuit, charging capacitors, and SCR, as described above in FIG. 5. The circuit 1000 includes a pulse width modulating (PWM) controller U3, which receives the charge and charge return signals from the charge circuit 912 of FIG. 9. When a pulse is directed to the circuit 1000 from the microcontroller U10, the PWM controller U3 generates pulse signals on output pins, which are passed through resistors R16, R65 to induce current through transformer T1 which is arranged with capacitor C16, resistor R7, and diode D12 to form a current on an opposite side of the transformer T1. Capacitors C20 and C21 are charged by the current induced through the transformer T1, and are discharged through pulse outputs (to a high voltage probe) on an opposite side of an approximately 25:1 step-up transformer T2 arranged to generate a high voltage pulse at the high voltage probe based on the charge on C20 and C21.

Additional components that can be incorporated in the circuit 1000 include a voltage rectifier U18, as well as indicators and other components leading to a comparator U5. The comparator U5 compares the high and low voltages to determine whether the capacitors are charged. Once the capacitors are charged, photocoupler U4 is activated indicating that the high voltage probe can be discharged.

Figure 11:
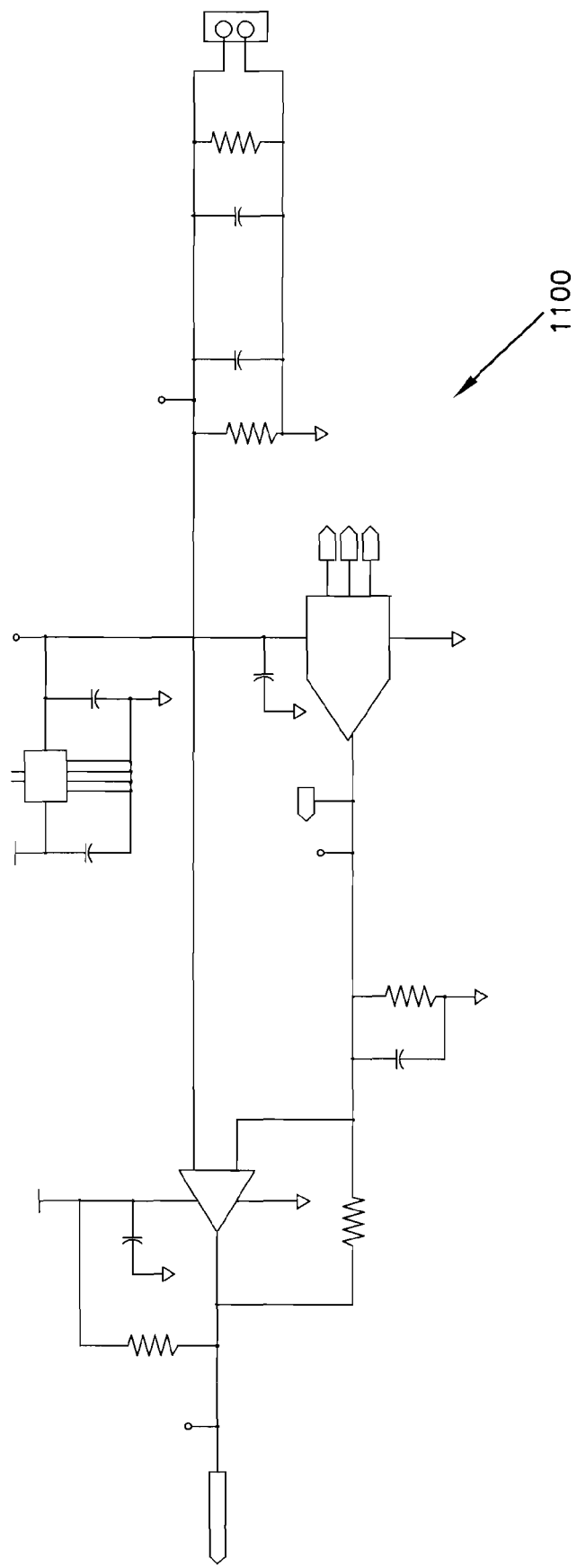
FIG. 11 is a further schematic view of a high voltage assembly useable in a tire defect tester, for use in accordance with the embodiment of FIG. 9.

As illustrated in FIG. 5, a signal is output from a high voltage probe and through a current transformer to detect the current. Referring now to FIG. 11, a return signal from a current transformer is received at connector J6, which passes that signal through a peak detector circuit formed from capacitors C29 and C30, resistors R36 and R37, and diode D15, forming an RC circuit. A D/A converter U8 (as powered via voltage regulator U13 and related capacitances C46, C47, C31) forms an analog signal from an input value for the expected threshold received at the current transformer, as indicated by control circuitry (e.g. received from the control circuitry of FIGS. 6-7). A comparator U7 compares the expected threshold from the converter U8 to the peak-detected signal received at J6, which is stored on the capacitors C29 and C30. The comparator U7 outputs a logic level corresponding to a time at which the voltage of the discharging capacitors remains above a threshold of approximately 1V to 1.2V. As previously mentioned, this logic level duration typically is about 2 ms, however it may vary depending upon the input energy to the high voltage probe and the element values of the resistors and capacitors in the peak detector RC circuit. The logic level output is passed back to the high voltage microcontroller U10 of FIG. 9, which compares the signal to an expected signal (e.g. a numerical time value) to determine whether a flaw exists at the current location on the tire. The microcontroller U10 can format a message and transfer fault information or other test data back to control circuitry via the RS-232 interface as well.

Figure 12:
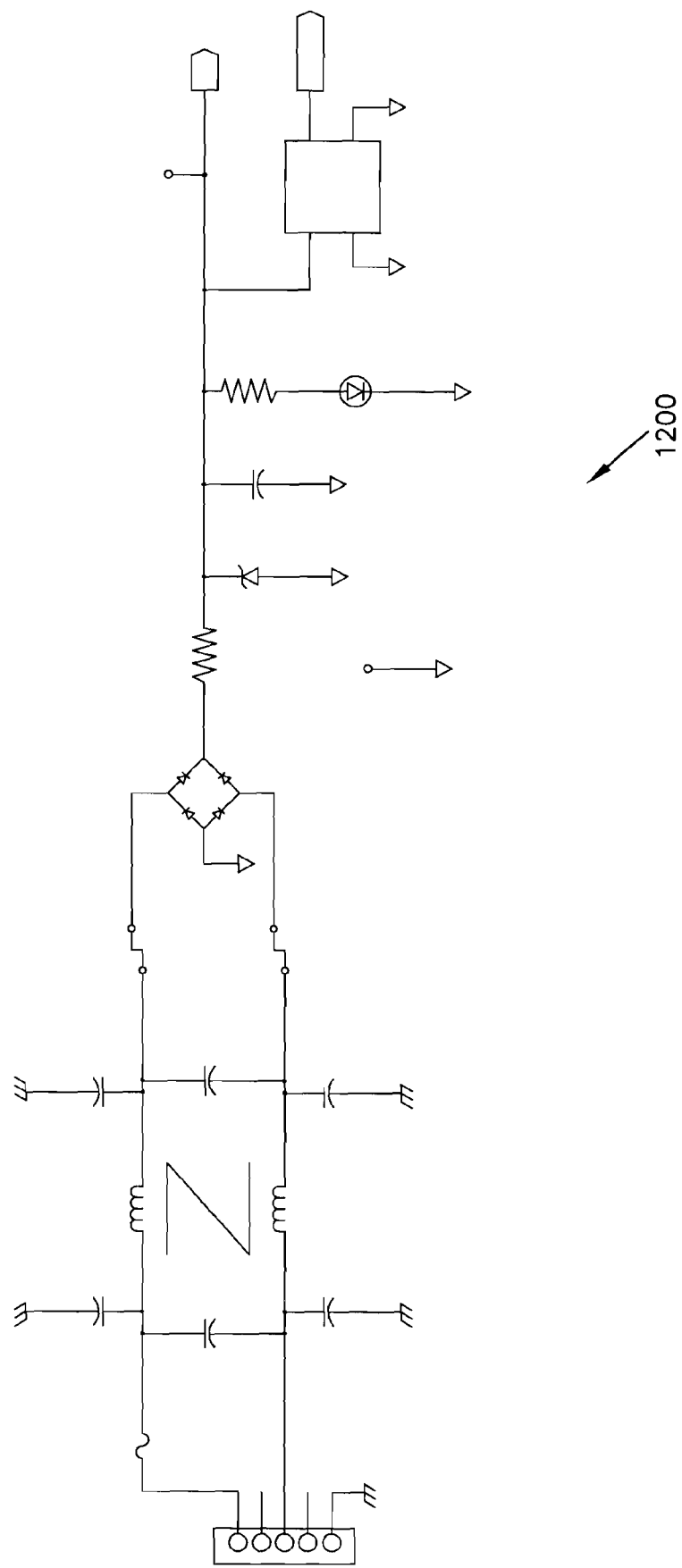
FIG. 12 is a schematic view of a power input circuit useable in conjunction with a high voltage assembly, as described in FIGS. 9-11.
Figure 13:
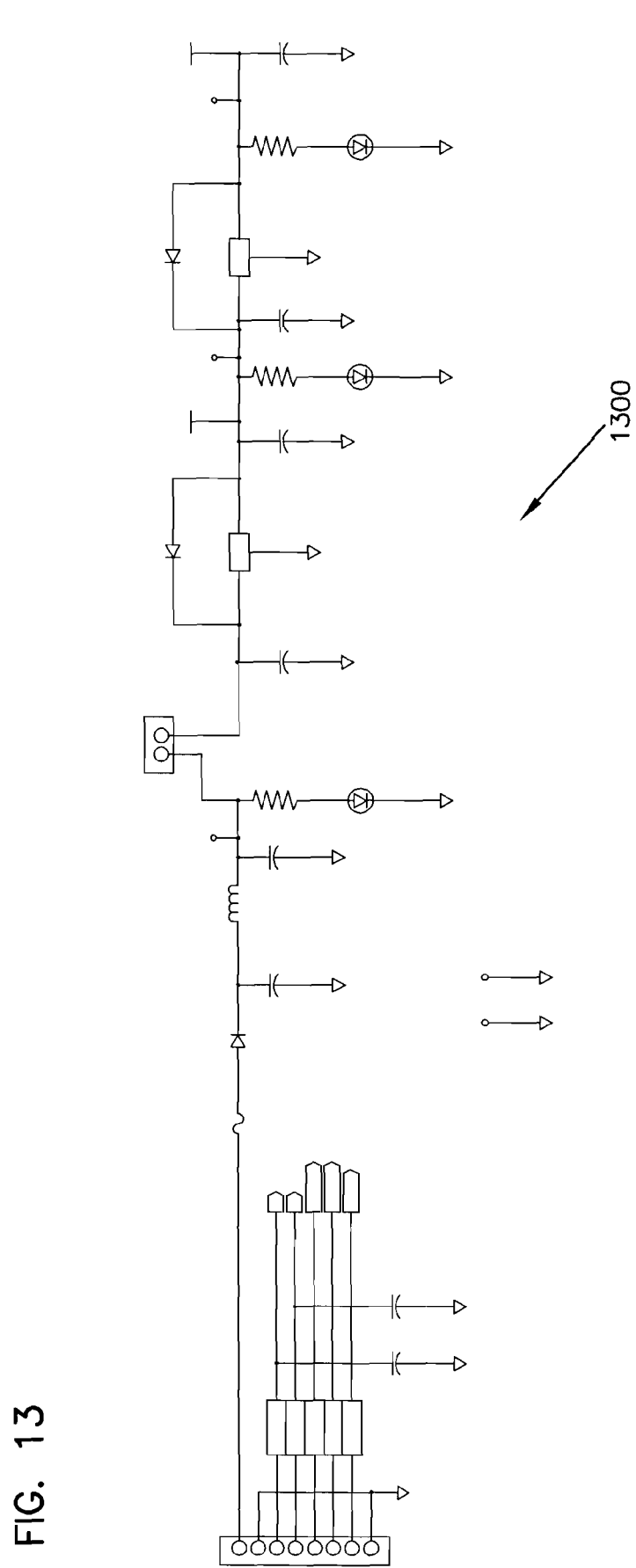
FIG. 13 is a schematic view of a control input circuit useable in conjunction with the high voltage assembly, as described in FIGS. 9-11.

FIGS. 12-13 provide signal conditioning for input voltages and control signals received into the circuitry of FIGS. 9-11. FIG. 12 illustrates a circuit 1200 that provides input conditioning for power signals used by the high voltage assembly. The circuit 1200 receives a high voltage signal at connector J1, which passes through a fuse F3 and across capacitors C3, C4 and transformer L1 to a pair of power relays K1B and K1C. The signal passes a bridge rectifier BR1 to prevent negative voltages. After the signal passes through resistor R1, it reaches an AC/DC converted U6 to form a 12 VDC output. Indicator and signal stabilizing circuitry D1, C5, R2, and D2 ensure a clean input signal to U6 and activate an indicator when voltage is present on the line.

FIG. 13 illustrates a circuit 1300 that receives DC voltage input and signal inputs at connector J3. In the embodiment shown, the RS-232 send and receive signals (Tx, Rx), as well as the manual, enable, and spare inputs pass directly through from the jumper with no additional conditioning (with the RS-232 signals capacitively coupled via capacitors C14 and C15 to a common voltage). When the control circuitry of FIGS. 6-7 is used in conjunction with the high voltage circuit of FIGS. 9-13, an RS-232 port (seen as IC3 of FIG. 7) provides data communication with microcontroller U10 of FIG. 9 to send pulse, threshold, and energy level commands to the high voltage circuit. Other messages can be exchanged via the RS-232 interface as well.

A DC voltage input is passed through fuse F4, diode D5, and past capacitors C8, C9, and inductor L3 to reach connector J2. Connector J2 allows jumpered enabling and disabling of the DC voltage, whose presence at J3 is indicated by LED D6. Additional capacitive couplings C10, C11, C12, and C13 are interspersed with voltage regulators U1 and U2. Additional LEDs D7, D8 and associated resistors R4 and R5 are used to indicated a presence of a voltage. Diodes D3, D4 are connected across the voltage regulators U1 and U2, respectively.

Referring now to FIGS. 9-13 generally, the high voltage circuits 900-1300 can be configured to receive commands via the RS-232 interface from the control circuit of FIGS. 6-7. These commands can include an input energy level to be generated by the high voltage probe, and an expected observed threshold energy at the current transformer opposite the probe. The expected observed threshold energy corresponds to a level above which a flaw is determined to exist.

Each pulse is independently directed to the high voltage circuits, which in turn generate a pulse on a high voltage probe and assess return voltage received (e.g. at comparator U7) to sense faults in a tire. In response to a sensed fault, the circuitry can output a return message to the control circuitry, which can store and catalog the sensed fault, halt a motor arranged to rotate the tire for analysis, or output additional pulses of the same or different values to validate the finding of a flaw in the tire. Through use of such a pulse-by-pulse system using pulses of differing energy levels, it is expected that various types of flaws (e.g. holes, separations, or other flaw types) can be detected and categorized in terms of observed response to differing energy levels.

In certain embodiments of the system, particularly those incorporating circuits analogous to the high voltage circuits 900-1300, statistical analysis of those flaws could be performed, either within the control circuitry, the high voltage circuitry (e.g. at U10), or within a computer communicatively connected to the tire tester. Flaw events can be stored in a memory associated with the tire tester or associated computer. These flaw events can be stored in a data record such as a flaw record, which includes an indication of the flaw, the tire on which the flaw is detected, the time at which the flaw is detected, the severity and type of the flaw, the location of the flaw on the tire, and raw data collected regarding the flaw (e.g. energy thresholds and observed capacitor discharge time). Additional tire and test information can be tracked as well, such as the model and size of the tire, an identifier of the tester performing the test, and other test settings. Subsequently, the stored flaw records can be examined to perform this statistical analysis. For example, flaw records can be used to correlate various data such as the location of a flaw (e.g. in the wall, tread, or other location), types of flaws, number of flaws per tire, number of flaws in a series of tires, number of flaws for a particular type of tire, or other measures. This information can allow a user to detect a recurring type of flaw or flaw location in a particular brand of tire or under typical use. For example, detection of a recurring type or location of a flaw in a common brand of tire under disparate usage conditions may correspond to a design problem in the tire. Such statistical analysis can also include analysis of responses to known flaws of differing types to determine expected energy level responses based on the type of flaw.

In certain embodiments, multiple tire defect testers can be used in combination, such as at a tire manufacturing, maintenance, or testing facility. In such instances, the tire defect testers can be communicatively networked, and data from multiple testers can be compiled in one of the testers or a database of a computing system connected to the network. In networked embodiments, this data can be analyzed centrally by a tester or computing system, and can be used to detect overall flaws in a tire testing, maintenance, or manufacturing process. Flaw records can also be used to halt or alter upstream actions on tires (e.g. manufacturing processes or maintenance actions), or can sound an alarm if flaws are detected at a greater than acceptable rate.

Additional circuitry and circuit routing can be incorporated into the systems described herein, such as the routing, signal conditioning, and signal/clock generation components shown in FIGS. 5-13. Although in FIGS. 5-13 and the corresponding detailed description, certain integrated circuits and discrete component values are described, other values can be used as well to provide functionality analogous to that described herein. Furthermore, other arrangements of circuits and components can be used to achieve the functionality described herein.

Referring generally to the systems described in FIGS. 5-13 above, in certain embodiments, the controllers described herein generate all time-based operations from a single frequency standard. Use of a single frequency standard ensures accurate timing for all functions, as compared to an analog time based controller. Digital control also provides consistency between control board assemblies, leading to a higher degree of interchangeability and less adjustments and set up time in the field.

In certain further embodiments, circuitry used in the controllers of the present disclosure make extensive use of surface mount technology. Use of surface mount technology reduces the size of the controller considerably and also permits machine assembly, reducing the chance of human error in assembly. The controller also takes advantage of changes in connector technology. Connections are made through field installable connectors, allowing both rapid installation and rapid change out of the control board, without the risk of incorrect wiring.

The controllers described in the present disclosure offer several advantages. For example, measuring the energy enables detecting and recording more information than merely detecting the presence or absence of a flaw. A controller reads the operator controls, runs the test sequence, measures, evaluates the results, and provides indications to the operator. Putting all of these functions under digital programmable control means the functions are not subject to environmental changes such as heat, humidity and age, which makes the operation more reliable and repeatable.

The above specification, examples and data provide a complete description of the manufacture and use of the composition of the invention. Since many embodiments of the invention can be made without departing from the spirit and scope of the invention, the invention resides in the claims hereinafter appended.

The invention claimed is:

1. A tire defect tester comprising
a first electrode arranged to direct energy toward a tire;
a second electrode arranged on an opposite side of the tire from the first electrode to receive energy passing through the tire from the first electrode;
a sensor electrically connected to the second electrode;
a fault indicator circuit responsive to the sensor and configured to indicate the presence of a flaw upon energy above a threshold level being sensed at the second electrode; and
a signal generator including:
    a capacitor arranged to discharge current upon electrical connection to the high voltage probe;
    a rectifier electrically connected to the capacitor and selectively connecting the capacitor to the high voltage probe; and
    a transformer electrically connected between the rectifier and the high voltage probe.

2. The tire defect tester of claim 1, wherein the first electrode includes a high voltage probe.

3. The tire defect tester of claim 2, further comprising a signal generator configured to periodically activate the first electrode.

4. The tire defect tester of claim 3, wherein the signal generator is a periodic signal generator and includes a relaxation oscillator.

5. The tire defect tester of claim 4, wherein the relaxation oscillator includes a spark gap, one or more resistors, and one or more capacitors.

6. The tire defect tester of claim 1 wherein the energy sensor is a current sensor.

7. The tire defect tester of claim 1, wherein the fault indicator circuit includes a capacitor arranged to store energy received from the energy sensor and a comparator arranged to compare the energy received on the capacitor to the threshold level.

8. The tire defect tester of claim 7, wherein the fault indicator circuit further includes a microcontroller configured to determine the presence of a flaw in the tire based on an output received from the comparator.

9. The tire defect tester of claim 1, further comprising a motor enabling signal, electrically connecting to a motor arranged to rotate the tire.

10. The tire defect tester of claim 1, further comprising a microcontroller arranged and configured to trigger high voltage pulses at the first electrode.

11. The tire defect tester of claim 10, wherein the microcontroller is further configured to store data records related to the tire.

12. The tire defect tester of claim 1, wherein the data records include flaw records having information regarding at least one of the location of the flaw on the tire, the type of flaw, the severity of the flaw, the tire having the flaw, and the time the flaw was detected.

13. The tire defect tester of claim 1, wherein the energy sensor includes an electrode placed at a position opposite the energy source.

14. The tire defect tester of claim 1, further comprising a flaw indicator arranged to be activated by a control assembly upon detection of a flaw in the tire.

15. The tire defect tester of claim 1, further comprising a tire type input received by a control assembly, the tire input regulating an energy level of a signal generated by the energy source.

16. A tire defect tester comprising
a first electrode arranged to direct energy toward a tire;
a second electrode arranged on an opposite side of the tire from the first electrode to receive energy passing through the tire from the first electrode;
a sensor electrically connected to the second electrode;
a fault indicator circuit responsive to the sensor and configured to indicate the presence of a flaw upon energy above a threshold level being sensed at the second electrode; and
one or more communication interfaces connecting a high voltage assembly to a control assembly, the high voltage assembly electrically connected to the energy source and the energy sensor.

17. The tire defect tester of claim 16, wherein the one or more communication interfaces are RS-232 interfaces.

18. The tire defect tester of claim 16, further comprising:
a pulse generator arranged to trigger a voltage pulse at a circuit output, the circuit output electrically connectable to the first electrode;
an energy sensor arranged to receive energy from a circuit input, the circuit input electrically connectable to the second electrode; and
a fault indicator circuit responsive to the energy sensor and configured programmed to indicate the presence of a flaw upon energy above a threshold level being sensed at the circuit input.

* * * * *

UNITED STATES PATENT AND TRADEMARK OFFICE
CERTIFICATE OF CORRECTION

PATENT NO. : 8,291,753 B2  Page 1 of 1
APPLICATION NO. : 12/129462
DATED : October 23, 2012
INVENTOR(S) : Range et al.

It is certified that error appears in the above-identified patent and that said Letters Patent is hereby corrected as shown below:

In the Specification:

Col. 10, line 59: "capacitors C1802 and" should read --capacitors C1 802 and--

Col. 10, line 64: "C1802 and C2 804 are" should read --C1 802 and C2 804 are--

Col. 11, line 19: "discharges C1802" should read --discharges C1 802--

In the Claims:

Col. 16, line 22, claim 12: "claim 1, wherein" should read --claim 11, wherein--

Col. 16, line 60, claim 18: "configured programmed to" should read --configured to--

Signed and Sealed this
Seventeenth Day of September, 2013

Teresa Stanek Rea
*Deputy Director of the United States Patent and Trademark Office*